United States Patent
Iu et al.

(10) Patent No.: US 10,351,583 B2
(45) Date of Patent: Jul. 16, 2019

(54) HIGHLY ISOSELECTIVE CATALYST FOR ALKENE HYDROFORMYLATION

(71) Applicant: Eastman Chemical Company, Kingsport, TN (US)

(72) Inventors: Leo Iu, Fife (GB); Matthew Clarke, Fife (GB); Kevin John Fontenot, Jonesborough, TN (US); Mesfin Ejerssa Janka, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 16/173,207

(22) Filed: Oct. 29, 2018

(65) Prior Publication Data

US 2019/0161508 A1 May 30, 2019

Related U.S. Application Data

(63) Continuation of application No. 15/824,347, filed on Nov. 28, 2017, now Pat. No. 10,144,751.

(51) Int. Cl.

| | |
|---|---|
| *C07C 45/50* | (2006.01) |
| *C07F 9/00* | (2006.01) |
| *B01J 31/00* | (2006.01) |
| *C07F 9/6571* | (2006.01) |
| *B01J 31/18* | (2006.01) |
| *B01J 31/24* | (2006.01) |

(52) U.S. Cl.
CPC ......... *C07F 9/6571* (2013.01); *B01J 31/1875* (2013.01); *B01J 31/2419* (2013.01); *C07C 45/50* (2013.01); *B01J 2231/321* (2013.01); *B01J 2531/822* (2013.01)

(58) Field of Classification Search
CPC .... C07C 45/50; C07F 9/6571; B01J 31/1875; B01J 31/2419
See application file for complete search history.

(56) References Cited

U.S. PATENT DOCUMENTS

| | | | | |
|---|---|---|---|---|
| 4,760,194 | A * | 7/1988 | Phillips | C07C 45/49 502/162 |
| 8,710,275 | B2 * | 4/2014 | Norman | C07C 45/50 502/102 |
| 9,308,527 | B2 | 4/2016 | How et al. | |
| 10,144,781 | B2 | 12/2018 | Iu et al. | |
| 10,183,963 | B2 | 1/2019 | Iu et al. | |

FOREIGN PATENT DOCUMENTS

| | | |
|---|---|---|
| WO | WO 2012/016147 A2 | 2/2012 |
| WO | WO 2014/016147 A2 | 1/2014 |

OTHER PUBLICATIONS

Noonan et al. An Asymmetric Hydroformylation Catalyst that Delivers Branched Aldehydes from Alkyl Alkenes. Angewandte Chemie, International Edition. vol. 51, 2477-2480 (Year: 2012).*
Noonan et al. Rhodium/phospholane-phosphite catalysts give unusually high regioselectivity in the enantioselective hydroformylation of vinyl arenes. Chemical Communications, vol. 50, 1475-1477. (Year: 2014).*
Dingwall, Paul et al.; "Understanding a Hydroformylation Catalyst that Produces Branched Aldehydes from Alkyl Alkenes"; Journal of the American Chemical Society; 2017; pp. 15921-15932; 139.
Hintermann, Lukas et al.; "Organocatalytic Stereoisomerization versus Alkene Isomerization: Catalytic Asymmetric Synthesis of 1-Hydroxy-trans-2,5-diphenylphospholane 1-Oxide"; Synthesis; 2013; pp. 309-325; 45.
Noonan, Gary M. et al.; "An Asymmetric Hydroformylation Catalyst that Delivers Branched Aldehydes from Alkyl Alkenes"; Angewandte Chemie; 2012; pp. 2477-2480; 51.
Riisager, A. et al.; "Propene hydroformylation by supported aqueous-phase Rh-NORBOS catalysts"; Journal of Molecular Catalysis A: Chemical: 2003; pp. 259-272; 193.
Noonan, Gary M., et al.; Rhodium/phospholane-phospite catalysts give unusually high regioselectivity in the enantioselective hydroformylation of vinyl arenes.; Chemical Communications, vol. 50, No. 12, pp. 1475-1477 (2014).
Notification of Transmittal of The International Search Report and The Written Opinion of the International Searching Authority, or the Declaration; International Application No. PCT/US2018/062522 with a filing date of Nov. 27, 2018.
Notification of Transmittal of The International Search Report and The Written Opinion of the International Searching Authority, or the Declaration; International Application No. PCT/US2018/062520 with a filing date of Nov. 27, 2018.

* cited by examiner

*Primary Examiner* — Sikarl A Witherspoon
(74) *Attorney, Agent, or Firm* — Kenrick L. Vidale

(57) ABSTRACT

Ligands for use with catalyst compositions used in hydroformylation reactions are described herein. The ligands are used with various octofluorotoluene or hydrocarbon solvents and achieve an increase in isoselectivity with an increase in temperature, an increase in TON with an increase in temperature, and/or will show isoselectivity that is surprisingly high in comparison to the hydroformylation reactions using common solvents.

25 Claims, 2 Drawing Sheets

HIGHLY ISOSELECTIVE CATALYST FOR ALKENE HYDROFORMYLATION

PARTIES TO JOINT RESEARCH AGREEMENT

Inventions disclosed or claimed herein were made pursuant to a Joint Research Agreement between Eastman Chemical Company and the University Court of the University of St. Andrews, a charitable body registered in Scotland.

BACKGROUND OF INVENTION

The hydroformylation reaction, also known as the oxo reaction, is used extensively in commercial processes for the preparation of aldehydes by the reaction of one mole of an olefin with one mole each of hydrogen and carbon monoxide. A particularly important use of the reaction is in the preparation of normal (n-) and butyraldehyde(iso-) from propylene. Both products are key building blocks for the synthesis of many chemical intermediates like alcohols, carboxylic acids, esters, plasticizers, glycols, essential amino acids, flavorings, fragrances, polymers, insecticides, hydraulic fluids, and lubricants.

At present, high n-selectivity is more easily achieved whereas achievement of high iso-selectivity remains challenging. Different approaches have been attempted throughout the years to tackle this problem, including the use of various ligands (Phillips, Devon, Puckette, Stavinoha, Vanderbilt, (Eastman Kodak Company), U.S. Pat. No. 4,760,194) and carrying out reactions under aqueous conditions (Riisager, Eriksen, Hjorkjaer, Fehrmann, J. Mol. Catal. A: Chem. 2003, 193, 259). The results have generally not been satisfactory, with either unimpressive iso-selectivity and/or because the reaction needs to be run at an undesirable temperature. The highest iso-selectivity reported was 63% in a reaction carried out at 19° C. (Norman, Reek, Besset, (Eastman Chemical Company), U.S. Pat. No. 8,710,275). However, in some instances this is not desirable because hydroformylation reactions conducted at lower temperatures may result in lower reaction rates, so carrying out the reaction at a higher temperature is generally preferred in industry. In this case, the iso-selectivity was reduced to 38% when the reaction was carried out at 80° C. Thus, there remains a need for catalysts with high iso-selectivity at temperatures above 19° C.

SUMMARY OF INVENTION

According to an embodiment, the disclosure teaches a process for preparing at least one aldehyde under hydroformylation temperature and pressure conditions. The process includes contacting at least one olefin, which in some embodiments may be propylene, with hydrogen and carbon monoxide in the presence of at least one solvent and a transition metal-based catalyst composition, which in some embodiments may be rhodium based, that includes a phospholane phosphite ligand. The ligand is represented by the following general formula:

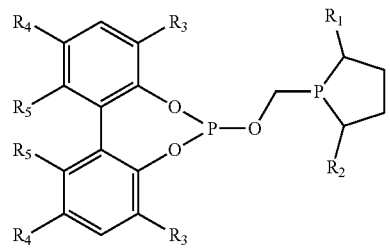

Wherein:

R1 and R2 are independently selected from substituted and unsubstituted, aryl, alkyl, aryloxy or cycloalkyl groups containing from 1 to 40 carbon atoms;

R3 and R4 are independently selected from substituted and unsubstituted, aryl, alkyl, alkoxy, trialkylsilyl, triarylsilyl, aryldialkylsilyl diarylalkylsilyl and cycloalkyl groups containing from 1 to 20 carbon atoms, wherein the silicon atom of the alkylsilyl is in the alpha position of the substituent; and R5 is independently selected from H, or alkyl group.

In an alternative embodiment, the ligand is represented by the following general formula:

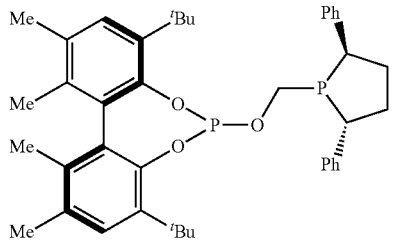

In alternative embodiments the process may be completed with phospholane phosphite ligands derived from achiral biphenol diol components. Representative examples include and are selected from the following ligands, (A) through (D), represented by their general formulas:

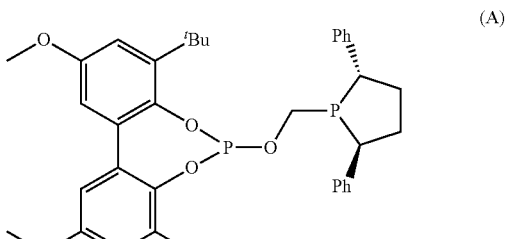

(A)

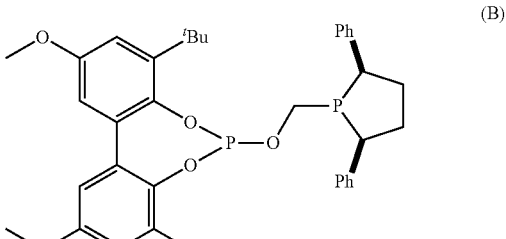

(B)

-continued

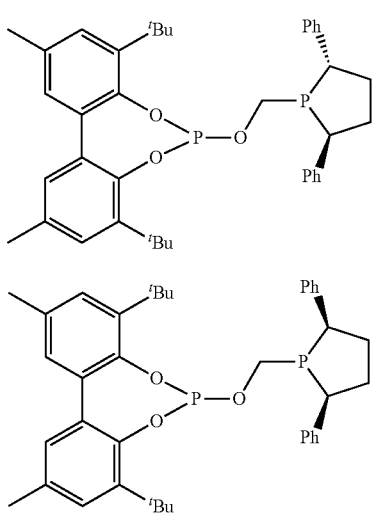

(C)

(D)

Regardless of ligand used, the process uses either fluorinated solvents which can be octofluorotoluene, or perfluorophenyl octyl ether or a hydrocarbon solvent which can be n-nonane, n-decane, n-undecane, or n-dodecane. The aldehyde product of the process comprising an iso-selectivity in some embodiments of about 55% to about 80%, about 55% to about 77%, about 58 to about 73%, about 60 to about 70%, or about 55% or greater.

In addition, the process operates in a pressure range in some embodiments of about 2 atm to about 80 atm, about 5 to about 70 atm, about 8 atm to about 20 atm, about 8 atm, or about 20 atm. The process also operates in a temperature range in some embodiments of about 40 to about 150 degrees Celsius, about 40 about 120 degrees Celsius, about 40 to about 100 degrees Celsius, about 50 about 90 degrees Celsius, about 50 degrees Celsius, about 75 degrees Celsius, or about 90 degrees Celsius.

The disclosure also provides transition metal-based catalyst composition which includes a phospholane phosphite ligand represented by the following general formula:

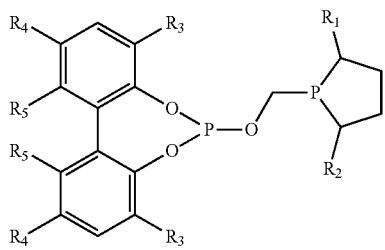

Wherein:
R1 and R2 are independently selected from substituted and unsubstituted, aryl, alkyl, aryloxy or cycloalkyl groups containing from 1 to 40 carbon atoms;
R3 and R4 are independently selected from substituted and unsubstituted, aryl, alkyl, alkoxy, trialkylsilyl, triarylsilyl, aryldialkylsilyl diarylalkylsilyl and cycloalkyl groups containing from 1 to 20 carbon atoms, wherein the silicon atom of the alkylsilyl is in the alpha position of the substituent; and
R5 is independently selected from H, or alkyl group.

In an alternative embodiment, the transition metal based catalyst composition which includes a phospholane phosphite ligand represented by the following general formula:

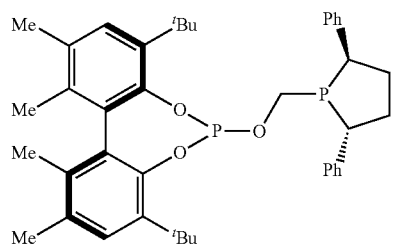

In yet another embodiment, transition metal-based catalyst composition which includes phospholane phosphite ligands derived from achiral biphenol diol components selected from the following ligands, (A) through (D), represented by their general formulas:

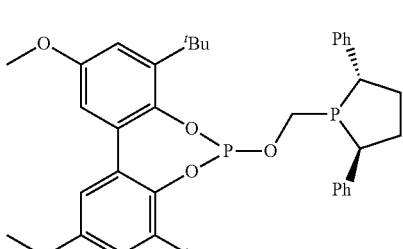

(A)

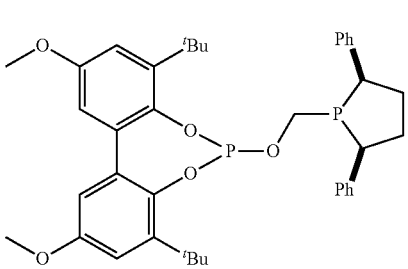

(B)

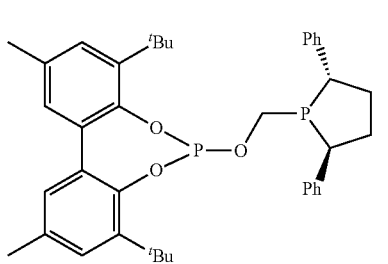

(C)

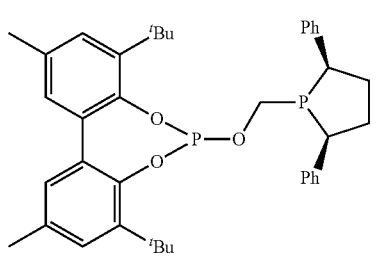

(D)

DETAILED DESCRIPTION

Figure 1:
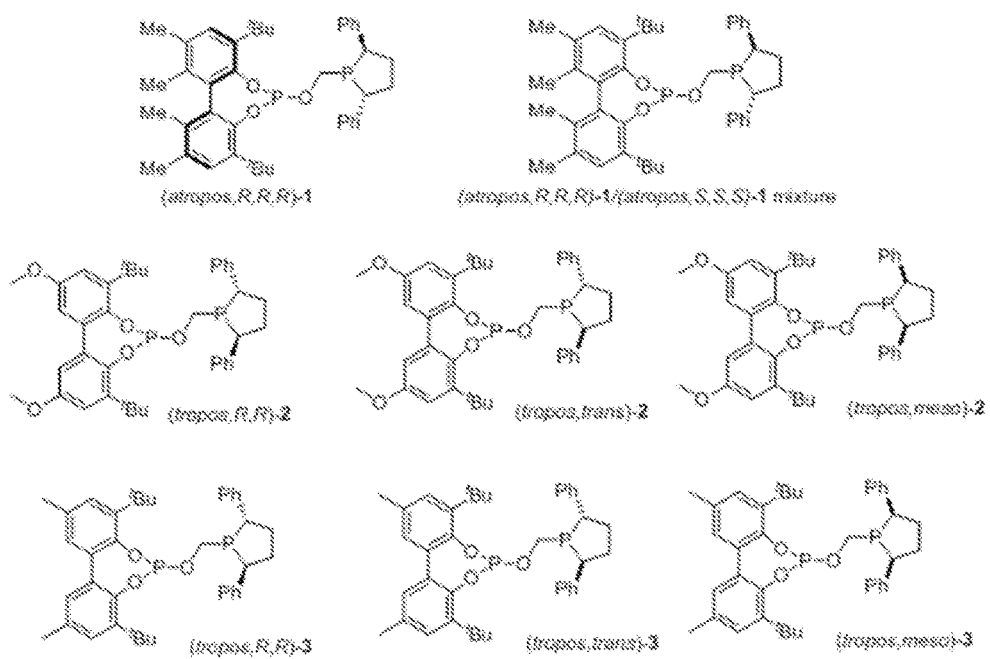
FIG. 1 illustrates the ligand compositions described herein.
Figure 2:
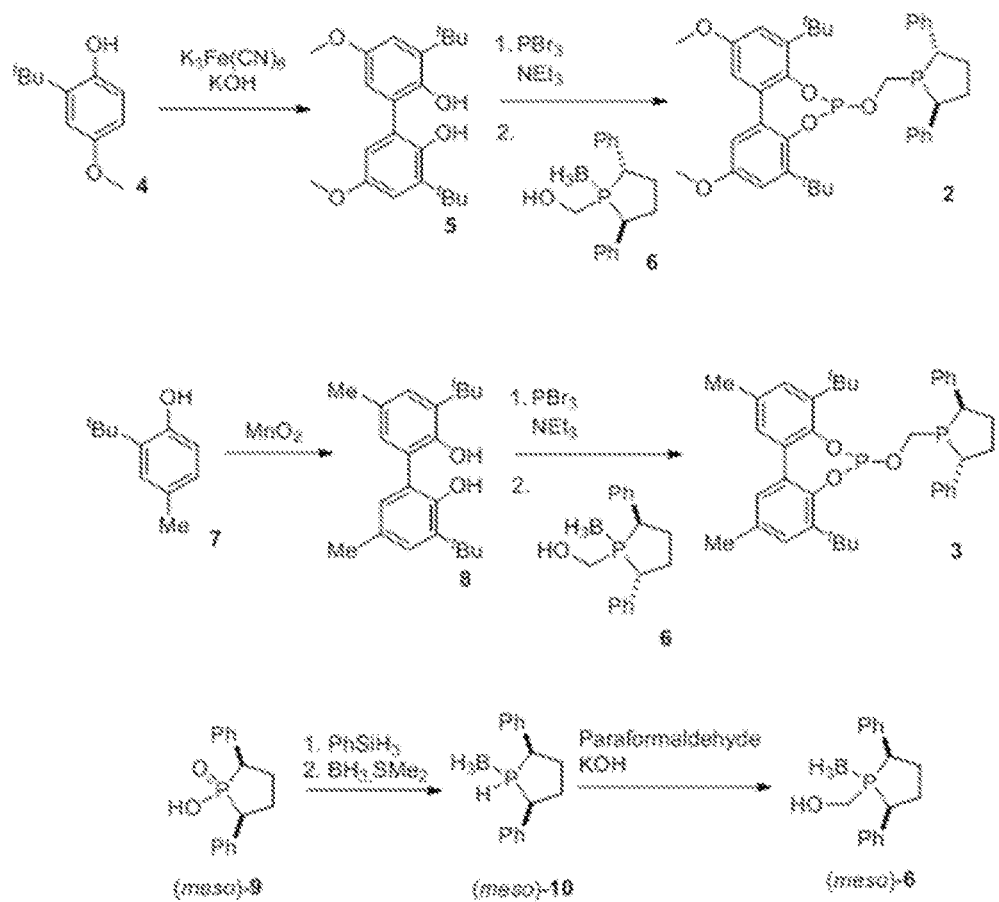
FIG. 2 illustrates the synthesis of various ligands and chemical structures described herein

This disclosure provides for a hydroformylation process for preparing at least one aldehyde, which includes contacting at least one olefin with hydrogen and carbon monoxide in the presence of at least one solvent and a transition metal-based catalyst composition comprising a phospholane phosphite ligand. Representative phospholane phosphite may be prochiral or achiral compositions and are represented the following general formula:

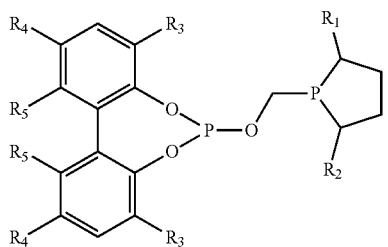

Wherein:

R1 and R2 are independently selected from substituted and unsubstituted, aryl, alkyl, aryloxy or cycloalkyl groups containing from 1 to 40 carbon atoms; and R3 and R4 are independently selected from substituted and unsubstituted, aryl, alkyl, alkoxy, trialkylsilyl, triarylsilyl, aryldialkylsilyl diarylalkylsilyl and cycloalkyl groups containing from 1 to 20 carbon atoms, wherein the silicon atom of the alkylsilyl is in the alpha position of the substituent R5 is independently selected from H, or alkyl group.

Beginning with $R^1$ and $R^2$, in some embodiments, one or both of $R^1$ and $R^2$ are independently selected from substituted or unsubstituted aryl groups. In some embodiments, the aryl group substituent on $R^1$, $R^2$ or both is a substituted or unsubstituted naphthyl or phenyl group. In some embodiments, the aryl group substituent on $R^1$, $R^2$ or both is a substituted or unsubstituted phenyl group. In some embodiments, the aryl group on $R^1$ and $R^2$ or both is a substituted phenyl group, in which the substituent is independently selected. In some embodiments, the aryl group on $R^1$ and $R^2$ or both is a substituted phenyl group, in which the substituent is independently selected from trifluoromethyl, trichloromethyl, cyano, sulfonic acid ester groups, carboxylic acid groups, carboxylic acid ester groups, salts of carboxylic acids, salts of sulfonic acids, quaternary ammonium groups, halogen atoms and nitro groups. In some embodiments, the substituents on the $R^1$ and $R^2$ are the same. In some embodiments, the substituents on both $R^1$ and $R^2$ are trifluoromethyl. In some embodiments, the substitution on the phenyl group is in a meta position with respect to the phosphorus atom to which the phenyl group is bound.

In some embodiments the $R^3$ and $R^4$ groups are independently selected from alkyl and trialkysilyl groups having one to four carbons. In some embodiments, all of the $R^3$ and $R^4$ groups are methyl. In some embodiments, all of the $R^3$ and $R^4$ groups are tert-butyl or trimethylsilyl. In some embodiments, all of the $R^3$ and $R^4$ groups are tert-butyl. In some embodiments, both of the $R^3$ groups are tert-butyl or trimethylsilyl and both of the $R^4$ groups are methyl. In some embodiments, both of the $R^3$ groups are tert-butyl both of the $R^4$ groups are methyl.

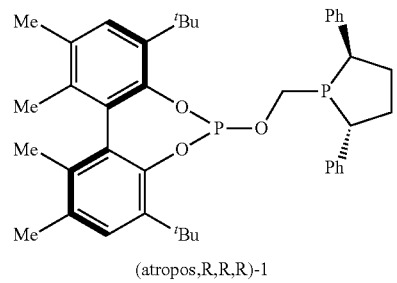

(atropos,R,R,R)-1

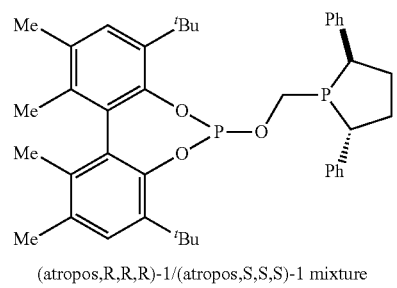

(atropos,R,R,R)-1/(atropos,S,S,S)-1 mixture

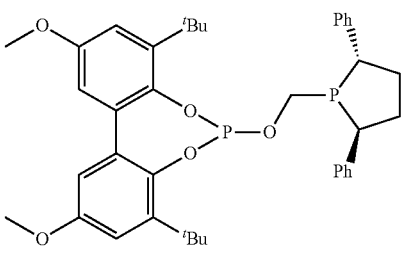

(tropos,R,R)-2

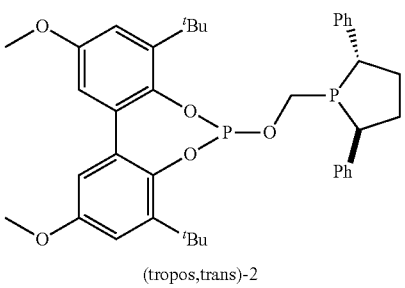

(tropos,trans)-2

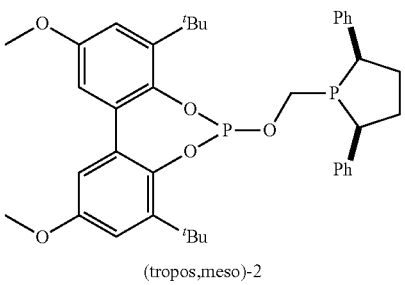

(tropos,meso)-2

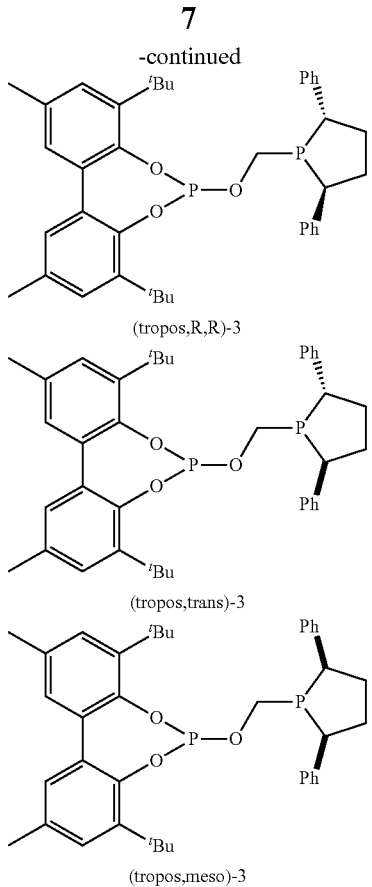

(tropos,R,R)-3

(tropos,trans)-3

(tropos,meso)-3

Specific formulations are represented by numbers (1) through (3) throughout herein and include the following ligands:

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10.

Notwithstanding that the numerical ranges and parameters setting forth the broad scope of the invention are approximations, the numerical values set forth in the specific examples are intended to be reported precisely in view of methods of measurement. Any numerical value, however, inherently contains certain errors necessarily resulting from the standard deviation found in their respective testing measurements.

It is to be understood that the mention of one or more process steps does not preclude the presence of additional process steps before or after the combined recited steps or intervening process steps between those steps expressly identified. Moreover, the denomination of process steps, ingredients, or other aspects of the information disclosed or claimed in the application with letters, numbers, or the like is a convenient means for identifying discrete activities or ingredients and the recited lettering can be arranged in any sequence, unless otherwise indicated.

As used herein, the singular forms "a", "an", and "the" include plural referents unless the context clearly dictates otherwise. For example, reference to a $C_n$ alcohol equivalent is intended to include multiple types of $C_n$ alcohol equivalents. Thus, even use of language such as "at least one" or "at least some" in one location is not intended to imply that other uses of "a", "an", and "the" excludes plural referents unless the context clearly dictates otherwise. Similarly, use of the language such as "at least some" in one location is not intended to imply that the absence of such language in other places implies that "all" is intended, unless the context clearly dictates otherwise.

As used herein the term "and/or", when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

The process described herein requires that an olefin is contacted with hydrogen and carbon monoxide in the presence of a transition metal catalyst and ligand. In an embodiment, the olefin is propylene. It also contemplated that additional olefins, such as, for example, butene, pentene, hexene, heptene, and octene could work in the process.

The resultant catalyst composition of the process contains a transition metal as well a ligand described herein. In some embodiments, the transition metal catalyst contains rhodium.

Acceptable forms of rhodium include rhodium (II) or rhodium (III) salts of carboxylic acids, rhodium carbonyl species, and rhodium organophosphine complexes. Some examples of rhodium (II) or rhodium (III) salts of carboxylic acids include di-rhodium tetraacetate dihydrate, rhodium(II) acetate, rhodium(II) isobutyrate, rhodium(II) 2-ethyl-hexanoate, rhodium(II) benzoate and rhodium(II) octanoate. Some examples of rhodium carbonyl species include [Rh(acac)(CO)$_2$], Rh$_4$(CO)$_{12}$, and Rh$_6$(CO)$_{16}$. An example of rhodium organophosphine complexes is tris(triphenylphosphine) rhodium carbonyl hydride may be used.

The absolute concentration of the transition metal in the reaction mixture or solution may vary from about 1 mg/liter up to about 5000 mg/liter; in some embodiments, it is higher than about 5000 mg/liter. In some embodiments of this invention, the concentration of transition metal in the reaction solution is in the range of from about 20 to about 300 mg/liter. Ratio of moles ligand to moles of transition metal can vary over a wide range, e.g., moles of ligand:moles of transition metal ratio of from about 0.1:1 to about 500:1 or from about 0.5:1 to about 500:1. For rhodium-containing catalyst systems, the moles of ligand:moles of rhodium ratio in some embodiments is in the range of from about 0.1:1 to about 200:1 with ratios in some embodiments in the range of from about 1:1 to about 100:1, or from about 1:1 to about 10:1.

In some embodiments, catalyst is formed in situ from a transition metal compound such as [Rh(acac)(CO)$_2$] and a ligand. It is appreciated by those skilled in the art that a wide variety of Rh species will form the same active catalyst when contacted with ligand, hydrogen and carbon monoxide, and thus there is no limitation on the choice of Rh pre-catalyst.

In additional embodiments, the process is carried out in the presence of at least one solvent. Suitable solvents include fluorinated solvents such as octofluorotoluene, or perfluorophenyl octyl ether or hydrocarbon solvents such as, for example, n-nonane, n-decane, n-undecane, and n-dodecane. It is also contemplated that other solvents may be used in combination with these solvents.

The disclosure further provides methods for the synthesis methods as generally described here and specifically described in the Examples below.

As for formulating the catalyst systems, no special or unusual techniques are required for preparing the catalyst systems and solutions of the present invention, although in some embodiments higher activity may be observed if all manipulations of the rhodium and ligand components are carried out under an inert atmosphere, e.g., nitrogen, argon and the like. Furthermore, in some embodiments it may be advantageous to dissolve the ligand and the transition metal together in a solvent to allow complexation of the ligand and transition metal followed by crystallization of the metal ligand complex as described in U.S. Pat. No. 9,308,527 which is herein incorporated by reference in its entirety.

Appropriate reaction conditions for effective hydroformylation conditions can be used as detailed in this paragraph. In some embodiments, the process is carried out at temperatures in the range of from about 40 to about 150 degrees Celsius, about 40 to about 120 degrees Celsius, about 40 to about 100 degrees Celsius, about 50 to about 90 degrees Celsius, about 50 degrees Celsius, about 75 degrees Celsius, or about 90 degrees Celsius. In some embodiments, the total reaction pressure may range from about 2 atm to about 80 atm, about 5 to about 70 atm, about 8 atm to about 20 atm, be about 8 atm, or be about 20 atm.

In some embodiments, the hydrogen:carbon monoxide mole ratio in the reactor may vary considerably ranging from about 10:1 to about 1:10 and the sum of the absolute partial pressures of hydrogen and carbon monoxide may range from about 0.3 to about 36 atm. In some embodiments, the partial pressure of hydrogen and carbon monoxide in the reactor is maintained within the range of from about 1 to about 14 atm for each gas. In some embodiments, the partial pressure of carbon monoxide in the reactor is maintained within the range of from about 1 to about 14 atm and is varied independently of the hydrogen partial pressure. The molar ratio of hydrogen to carbon monoxide can be varied widely within these partial pressure ranges for the hydrogen and carbon monoxide. The ratios of the hydrogen to carbon monoxide and the partial pressure of each in the synthesis gas (syngas-carbon monoxide and hydrogen) can be readily changed by the addition of either hydrogen or carbon monoxide to the syngas stream.

The amount of olefin present in the reaction mixture also is not critical. In some embodiments of the hydroformylation of propylene, the partial pressures in the vapor space in the reactor are in the range of from about 0.07 to about 35 atm. In some embodiments involving the hydroformylation of propylene, the partial pressure of propylene is greater than about 1.4 atm, e.g., from about 1.4 to about 10 atm. In some embodiments of propylene hydroformylation, the partial pressure of propylene in the reactor is greater than about 0.14 atm.

Any effective hydroformylation reactor designs or configurations may be used in carrying out the process provided by the present invention. Thus, a gas-sparged, liquid overflow reactor or vapor take-off reactor design as disclosed in the examples set forth herein may be used. In some embodiments of this mode of operation, the catalyst which is dissolved in a high boiling organic solvent under pressure does not leave the reaction zone with the aldehyde product taken overhead by the unreacted gases. The overhead gases then are chilled in a vapor/liquid separator to condense the aldehyde product and the gases can be recycled to the reactor. The liquid product is let down to atmospheric pressure for separation and purification by conventional technique. The process also may be practiced in a batchwise manner by contacting propylene, hydrogen and carbon monoxide with the present catalyst in an autoclave.

A reactor design where catalyst and feedstock are pumped into a reactor and allowed to overflow with product aldehyde, i.e. liquid overflow reactor design, is also suitable. In some embodiments, the aldehyde product may be separated from the catalyst by conventional means such as by distillation or extraction and the catalyst then recycled back to the reactor. Water soluble aldehyde products can be separated from the catalyst by extraction techniques. A trickle-bed reactor design also is suitable for this process. It will be apparent to those skilled in the art that other reactor schemes may be used with this invention.

For continuously operating reactors, it may be desirable to add supplementary amounts of the ligand (compound) over time to replace those materials lost by oxidation or other processes. This can be done by dissolving the ligand into a solvent and pumping it into the reactor as needed. The solvents that may be used include compounds that are found in the process such as olefin, the product aldehydes, condensation products derived from the aldehydes, and other esters and alcohols that can be readily formed from the product aldehydes. Example solvents include butyraldehyde, isobutyraldehyde, propionaldehyde, 2-ethylhexanal, 2-ethylhexanol, n-butanol, isobutanol, isobutyl isobutyrate, isobutyl acetate, butyl butyrate, butyl acetate, 2,2,4-trimethylpentane-1,3-diol diisobutyrate, n-butyl 2-ethylhexanoate, octofluorotoluene, perfluorophenyl octyl ether, n-nonane, n-decane, n-undecane, and n-dodecane. Ketones such as cyclohexanone, methyl isobutyl ketone, methyl ethyl ketone, diisopropylketone, and 2-octanone may also be used as well as trimeric aldehyde ester-alcohols such as Texanol™ ester alcohol (2,2,4-trimethyl-1,3-pentanediol mono (2-methylpropanoate)).

In some embodiments, the reagents employed for the invention hydroformylation process are substantially free of materials which may reduce catalyst activity or completely deactivate the catalyst. In some embodiments, materials such as conjugated dienes, acetylenes, mercaptans, mineral acids, halogenated organic compounds, and free oxygen are excluded from the reaction.

This invention can be further illustrated by the following examples of embodiments thereof, although it will be understood that these examples are included merely for purposes of illustration and are not intended to limit the scope of the invention unless otherwise specifically indicated.

EXAMPLES

Studies on rhodium-catalyzed propylene hydroformylation using (atropos,R,R,R)-1 ligand with different solvents and at different temperatures and pressures are reported in Table 1 (Comparative Examples), Table 2, Table 3 and Table 4. Both the iso- and n-aldehyde products were calibrated against an internal standard of 1-methylnaphthalene with gas chromatography (GC). The amount of both products from a reaction can be calculated to give the iso- to n-ratio and the productivity of the catalyst can be quantified using the turn over number (TON). TON refers to the relationship between the catalyst loading and the amount of product formed using the equation; TON=(iso-+n-aldehyde) (mmol)/[Rh(acac) $(CO)_2$] (mmol). The relative reactivities of catalysts between reactions can then be compared. For a reaction carried out at 90° C., a single charge of gas (10% propylene, 45% CO, 45% $H_2$) at a pressure of 20 bar, in the equipment used, the maximum TON, corresponding to 100% conversion, is ~1450. Reactions described here at different pressure and temperature will have different maximum theoretical turnover numbers. Moderate iso-selectivities were achieved (<60%) when the reactions were carried out in common solvents such as toluene, as shown in Table 1. An increase in iso-selectivity was observed when a lower pressure was applied. An increase in reaction temperature also lead to a decrease in iso-selectivity.

TABLE 1

Propylene hydroformylation using (atropos,R,R,R)-1 in common solvents

| Ex. | Solvent | Temp (° C.) | Pressure (atm) | Time (hr) | TON | % iso |
|---|---|---|---|---|---|---|
| 1 | Toluene | 50 | 8 | 16 | 784 | 57.2 |
| 2 | Toluene | 50 | 20 | 16 | 1348 | 54.5 |
| 3 | Toluene | 75 | 8 | 1 | 512 | 56.4 |
| 4 | Toluene | 75 | 20 | 1 | 1131 | 53.3 |
| 5 | Toluene | 90 | 8 | 1 | 500 | 56.0 |
| 6 | Toluene | 90 | 20 | 1 | 782 | 48.9 |
| 7 | n-Pentanal | 50 | 8 | 16 | 122 | 54.1 |
| 8 | Chlorobenzene | 50 | 8 | 16 | 755 | 56.5 |
| 9 | Texanol | 50 | 8 | 16 | 692 | 48.3 |

L:Rh = 1.25:1

In Table 1, propylene hydroformylation using (atropos,R,R,R)-1 ligand/Rh showed higher iso-selectivity when the reaction was carried out at lower temperature and lower pressure as predicted in conventional solvents. These conditions were not favorable for industry as industry prefers to operate reactions at higher temperatures and achieve either higher TON or higher isoselectivity. Hence, alternative solvents were required to accommodate industrially relevant conditions. Additionally, the common solvents utilized do not demonstrate isoselectivity above 57%.

In contrast, Tables 2, 3 and 4 below will show, in some cases, an increase in isoselectivity with an increase in temperature, an increase in TON with an increase in temperature, and/or will show isoselectivity that is surprisingly high in comparison to the propylene hydroformylation results in Table 1 using (atropos,R,R,R)-1 ligand in common solvents.

TABLE 2

Propylene hydroformylation using octofluorotoluene solvent using (atropos,R,R,R)-1 ligand

| Ex. | Solvent | Temp (° C.) | Pressure (atm) | Time (hr) | TON | % iso |
|---|---|---|---|---|---|---|
| 10 | Octafluorotoluene | 50 | 8 | 16 | 788 | 76.7 |
| 11 | Octafluorotoluene | 75 | 8 | 1 | 490 | 73.4 |
| 12 | Octafluorotoluene | 75 | 20 | 1 | 1020 | 58.8 |
| 13 | Octafluorotoluene | 90 | 8 | 1 | 550 | 64.7 |
| 14 | Octafluorotoluene | 90 | 20 | 1 | 1447 | 55.1 |

L:Rh = 1.25:1

TABLE 3

Propylene hydroformylation using perfluorophenyl octyl ether solvent using (atropos,R,R,R)-1 ligand

| Ex. | Solvent | Temp (° C.) | Pressure (atm) | Time (hr) | TON | % iso |
|---|---|---|---|---|---|---|
| 15 | Perfluorophenyl octyl ether | 90 | 20 | 1 | 1257 | 66.7 |
| 16 | Perfluorophenyl octyl ether | 75 | 20 | 1 | 674 | 70.3 |
| 17 | Perfluorophenyl octyl ether | 50 | 8 | 16 | 608 | 73.6 |

L:Rh 1.25:1

TABLE 4

Propylene hydroformylation using hydrocarbon solvents using (atropos,R,R,R)-1 ligand

| Ex. | Solvent | Temp (° C.) | Pressure (atm) | Time (hr) | TON | % iso |
|---|---|---|---|---|---|---|
| 18 | n-nonane | 50 | 8 | 16 | 624 | 70.4 |
| 19 | n-nonane | 90 | 20 | 1 | 1150 | 61.7 |
| 20 | n-decane | 50 | 8 | 16 | 641 | 70.8 |
| 21 | n-decane | 90 | 20 | 1 | 1335 | 54.2 |
| 22 | n-undecane | 50 | 8 | 16 | 640 | 70.8 |
| 23 | n-undecane | 75 | 8 | 1 | 442 | 66.4 |
| 24 | n-undecane | 75 | 20 | 1 | 680 | 68.3 |
| 25 | n-undecane | 82 | 20 | 1 | 887 | 66.7 |
| 26 | n-undecane | 90 | 8 | 1 | 508 | 61.2 |
| 27 | n-undecane | 90 | 20 | 1 | 1276 | 62.7 |
| 28 | n-dodecane | 50 | 8 | 16 | 675 | 70.3 |
| 29 | n-dodecane | 90 | 20 | 1 | 1497 | 60.1 |

L:Rh = 1.25:1

(atropos,R,R,R)-1 Ligand 1 is enantiomerically pure and therefore requires a lengthy synthesis and separation of enantiomers since it was designed for the hydroformylation of prochiral alkenes. For achiral propene, a ligand that is not enantiomerically pure would be economically attractive. Ligand 1 derivatives with reduced chirality elements were designed to reduce the synthetic cost.

Ligands 2 and 3 are derived from a diol, which rather than using a single enantiomer with axial chirality, described as atropos (tropos is Greek to turn; atropos—not to turn) as in ligand 1, make use of a tropos diol that that is not configurationally stable. Since resolution of enantiomer is not necessary, this type of diol is obtainable at significantly lower cost and more readily available. Tropos, trans-2 and tropos, trans-3 not only contain the phosphite unit derived from the achiral diol, but feature a phospholane ring that is a single trans diastereoisomer, but racemic (i.e. (R,R)/(S,S)), further reducing cost and increasing synthetic accessibility. Different isomers of these ligands (ligands 2 and 3) were tested and the results are shown in Tables 5 and 6.

Ligands that are not enantiomerically pure (Ligands 2 and 3) when used in octofluorotoluene or perfluorophenyl ether or a hydrocarbon as a solvent also give high iso-selectivity and in Tables 5 and 6 below either demonstrate an increase in isoselectivity with an increase in temperature or an increase in TON with an increase in temperature.

TABLE 5

Propylene hydroformylation using ligands 2 and 3 using L:Rh of 1.25:1

| Ex. | Ligand | Solvent | Temp (° C.) | Pressure (atm) | Time (hr) | TON | % iso |
|---|---|---|---|---|---|---|---|
| 30 | (tropos,R,R)-2 | Octafluorotoluene | 50 | 8 | 16 | 591 | 69.5 |
| 31 | (tropos,R,R)-2 | Octafluorotoluene | 75 | 8 | 1 | 446 | 59.9 |
| 32 | (tropos,R,R)-2 | n-Undecane | 75 | 20 | 1 | 905 | 64.9 |
| 33 | (tropos,R,R)-2 | n-Undecane | 90 | 20 | 1 | 1364 | 58.8 |
| 34 | (tropos,trans)-2 | Octafluorotoluene | 50 | 8 | 16 | 573 | 71.9 |
| 35 | (tropos,trans)-2 | n-Undecane | 75 | 20 | 1 | 1399 | 52.4 |
| 36 | (tropos,trans)-2 | n-Undecane | 90 | 20 | 1 | 1438 | 54.5 |
| 37 | (tropos,meso)-2 | Octafluorotoluene | 50 | 8 | 16 | 712 | 50.3 |
| 38 | (tropos,meso)-2 | n-Undecane | 75 | 20 | 1 | 985 | 49.3 |
| 39 | (tropos,R,R)-3 | Octafluorotoluene | 50 | 8 | 16 | 666 | 73.4 |
| 40 | (tropos,R,R)-3 | n-Undecane | 75 | 20 | 1 | 1341 | 53.1 |
| 41 | (tropos,R,R)-3 | n-Undecane | 90 | 20 | 1 | 1405 | 57.2 |
| 42 | (tropos,trans)-3 | Octafluorotoluene | 50 | 8 | 16 | 670 | 53.8 |
| 43 | (tropos,trans)-3 | n-Undecane | 75 | 20 | 1 | 1465 | 53.5 |
| 44 | tropos,trans)-3 | n-Undecane | 90 | 20 | 1 | 1506 | 54.7 |
| 45 | (tropos,meso)-3 | Octafluorotoluene | 50 | 8 | 16 | 487 | 51.9 |
| 46 | (tropos,meso)-3 | n-Undecane | 75 | 20 | 1 | 1081 | 48.5 |

L:Rh = 1.25:1

TABLE 6

Propylene hydroformylation using ligands 2 and 3 using L:Rh of 2:1

| Ex. | Ligand | Solvent | Temp (° C.) | Pressure (atm) | Time (hr) | TON | % iso |
|---|---|---|---|---|---|---|---|
| 47 | (tropos,R,R)-2 | n-Undecane | 75 | 20 | 1 | 877 | 67.9 |
| 48 | (tropos,R,R)-2 | Perfluorophenyl octyl ether | 75 | 20 | 1 | 748 | 67.8 |
| 49 | (tropos,trans)-3 | Octafluorotoluene | 50 | 8 | 16 | 922 | 74.2 |
| 50 | (tropos,trans)-3 | n-Undecane | 75 | 20 | 1 | 935 | 66.8 |
| 51 | (tropos,trans)-3 | n-Undecane | 90 | 20 | 1 | 1241 | 64.3 |
| 52 | (tropos,trans)-3 | Perfluorophenyl octyl ether | 75 | 20 | 1 | 898 | 60.7 |

A diasteromerically pure but racemic mixture ligand ((atropos,R,R,R)-1/(atropos,S,S,S)-1) when used in a hydrocarbon as a solvent also give high iso-selectivity as shown in Table 7.

TABLE 7

Propylene hydroformylation using ((atropos,R,R,R)-1/(atropos,S,S,S)-1) ligand

| Ex. | Solvent | Temp (° C.) | Pressure (atm) | Time (hr) | TON | % iso |
|---|---|---|---|---|---|---|
| 53 | n-Undecane | 90 | 20 | 1 | 1322 | 64.6 |
| 54 | n-Undecane | 75 | 20 | 1 | 818 | 67.9 |

L:Rh = 1.25:1

Examples of hydroformylation reactions utilizing the ligands disclosed herein are further described below as well as the synthesis of various ligands and chemical structures described herein.

All manipulations were carried out under an inert atmosphere of nitrogen or argon using standard Schlenk techniques. Dry and degassed solvents were obtained from a solvent still or SPS solvent purification system. Triethylamine and $CDCl_3$ were dried and degassed before use. n-pentanal, chlorobenzene, toluene, octafluorotoluene, perfluorophenyl octyl ether, n-nonane, n-decane, n-undecane, n-dodecane, 2,2,4-trimethyl-1,3-pentanediol monoisobutyrate, were degassed only before use. All chemicals, unless specified, were purchased commercially and used as received. $CO/H_2$ (1:1) and propylene/$CO/H_2$ (10:45:45) were obtained pre-mixed from BOC.

NMR spectra were recorded on a Bruker Advance 300, 400 or 500 MHz instrument. Proton chemical shifts are referenced to internal residual solvent protons. Carbon chemical shifts are referenced to the carbon signal of the deuterated solvent. Signal multiplicities are given as s (singlet), d (doublet), t (triplet), q (quartet), m (multiplet), br.s (broad singlet) or a combination of the above. Where appropriate coupling constants (J) are quoted in Hz and are reported to the nearest 0.1 Hz. All spectra were recorded at room temperature and the solvent for a spectrum is given in parentheses. NMR of compounds containing phosphorus were recorded under an inert atmosphere in dry and degassed solvent.

Mass spectrometry was performed on a Micromass GCT spectrometer, Micromass LCT spectrometer, Waters ZQ4000, Thermofisher LTQ Orbitrap XL or Finnigan MAT 900 XLT instruments.

Gas chromatography was performed on an Agilent Technologies 7820A machine.

Flash column chromatography was performed using dry and degassed solvents under an inert atmosphere using either Merck Geduran Si 60 (40-63 μm) silica gel or Sigma Aldrich activated neutral Brockmann I alumina.

Thin layer chromatographic (TLC) analyses were carried out using POLYGRAM SIL G/UV254 or POLYGRAM ALOX N/UV254 plastic plates. TLC plates were visualized using a UV visualizer or stained using potassium permanganate dip followed by gentle heating. Preparative TLC was performed on aluminum oxide glass plates with fluorescent indicator 254 nm.

General Procedure for Hydroformylations:

Hydroformylation reactions were carried out in Parr 4590 Micro Bench Top Reactors, having a volume capacity of 0.1 L, an overhead stirrer with gas entrainment head (set to 1200 RPM), temperature controls, pressure gauge and the ability to be connected to a gas cylinder.

The following general procedures were followed in each experiment.

[Rh(acac)(CO)$_2$] stock solution was prepared by dissolving 10.0 mg of [Rh(acac)(CO)$_2$] in 5.0 mL of toluene.

In a Schlenk flask under $N_2$ (or Argon) an appropriate ligand (6.40 μmol or 10.24 μmol), along with 0.65 mL of rhodium catalyst solution containing 5.12 μmol of [Rh(acac)(CO)$_2$] from the above stock solution and internal standard (1-methylnaphthalene) (0.1 mL) were dissolved in 19.35 mL of appropriate solvent to result in a molar ratio of Rh:ligand of 1:1.25 or Rh:ligand of 2.

An empty autoclave was sealed and flushed 3 times with 5-10 atm syngas (CO/H$_2$ 1:1), which was released to 1 atm each time. Then 20 mL of the solution from the Schlenk flask was added via the injection port. The resulting catalyst solution was activated by stirring at reaction temperatures and pressures specified in Tables 1-7 using syngas for one hour. The autoclave pressure was released and re-pressurized with propylene/CO/Hz (10:45:45) gas mix. The reaction was left stirring at reaction temperature for a length of time specified in the tables. After completion of the reaction the reactor was cooled to room temperature and the reactor pressure was released. The sample was then analyzed by gas chromatography (GC) with both isomers calibrated against 1-methylnaphthalene as an internal standard. GC results were used to determine the TOF (or TON when reaction time was longer than one hour) and iso-selectivity, which is the percentage of isobutyraldehyde to total butyraldehydes products.

Ligands Synthesis:

(atropos,R,R,R)-1 ligand was synthesized following literature procedures (Noonan, Fuentes, Cobley, Clarke, Angew. Chem. Int. Ed. 2012, 51, 2477) herein incorporated by reference in its entirety.

Synthesis of 3,3'-di-tert-butyl-5,5'-dimethoxy-1,1'-biphenyl-2,2'-diol 5

The commercially available 2-(tert-butyl)-4-methoxyphenol 4 (2.00 g, 11.10 mmol) was dissolved in methanol (60 mL). To this was added a solution of potassium hydroxide (1.25 g, 22.19 mmol) and potassium ferricyanide (3.65 g, 11.10 mmol) in water (60 mL) slowly, over a period of 1 hour. Upon addition, the reaction was stirred at room temperature for 1 hour. The reaction mixture was partitioned between ethyl acetate (100 mL) and water (40 mL). The organic products were collected and the aqueous layer was washed with ethyl acetate (2×50 mL). The organic products in ethyl acetate/methanol were combined, washed with brine, dried using magnesium sulfate and concentrated in vacuo. The resultant solid was washed with hexane to afford compound 5 as a white solid (1.31 g, 3.65 mmol, 66%). $^1$H NMR (CDCl$_3$, 400 MHz) δ 6.99 (d, J=3.1 Hz, 2H, 2×Ar—H), 6.66 (d, J=3.1 Hz, 2H, 2×Ar—H), 5.07 (s, 2H, 2×OH), 3.80 (s, 6H, 2×O—CH$_3$), 1.46 (s, 18H, 2×C(CH$_3$)$_3$). $^{13}$C NMR (CDCl$_3$, 101 MHz) δ 153.20 (s, 2C, 2×ArC—OCH$_3$), 145.90 (s, 2C, 2×ArC—OH), 138.94 (s, 2C, 2×ArC—C(CH$_3$)$_3$), 123.21 (s, 2C, 2×ArC—ArC), 115.28 (s, 2C, 2×ArCH), 111.75 (s, 2C, 2×ArCH), 55.75 (s, 2C, 2×O—CH$_3$), 35.19 (s, 2C, 2×C(CH$_3$)$_3$), 29.51 (s, 6C, 2×C(CH$_3$)$_3$). HRMS (ES$^+$) C$_{22}$H$_{30}$O$_4$— [M+Na]$^+$ m/z: 381.2028 found, 381.2042 required.

(trans-Rac)-6 and (R,R)-6 were synthesized following literature procedures (Noonan, Fuentes, Cobley, Clarke, Angew. Chem. Int. Ed. 2012, 51, 2477).

Synthesis of borane-protected-((meso)-2,5-diphenylphospholane 10, (meso)-10

Compound (meso)-10 was synthesized following literature procedures (L. Hintermann, M. Schmitz, O. V. Maltsev, P. Naumov, Synthesis, 2013, 45, 308-325) herein incorporated by reference in its entirety.

Unless stated otherwise, the procedure was carried out under Ar. Compound (meso)-9 (0.66 g, 2.43 mmol) was suspended in toluene (10 mL) and phenylsilane (0.52 g, 4.86 mmol) was added and the mixture was heated to reflux for 16 hours. The reaction was allowed to cool to room temperature and borane dimethyl sulfide complex (0.23 mL, 2.43 mmol) was added and the reaction was left to stir at room temperature for 24 hours. The reaction mixture was filtered through a short pad of silica gel (silica 60, 40-63 μm), eluted with toluene. The filtrate was concentrated in vacuo to afford a crude solid. The crude product was purified by column chromatography on silica gel (silica 60, 40-63 μm) using 0-5% diethyl ether in hexane as eluent to afford compound (meso)-10 as a white solid (0.31 g, 1.20 mmol, 49%). $^1$H NMR (CDCl$_3$, 500 MHz) δ 9.71 (s, 1H, POOH), 7.26-7.08 (m, 10H, Ar—H), 3.33-3.02 (m, 2H, 2×P—CH—Ar), 2.45-2.18 (m, 4H, 2×CH—CH$_2$). $^{13}$C NMR (101 MHz, CDCl$_3$) δ 135.90 (s, 2C, ArC), 128.36 (s, 2C, ArCH), 128.35 (s, 2C, ArCH), 128.14 (s, 2C, ArCH), 128.09 (s, 2C, ArCH), 126.57 (s, ArCH), 126.55 (s, ArCH), 43.18 (d, J=86.0 Hz, 2C, CH—P), 27.95 (s, CH—CH$_2$), 27.80 (s, CH—CH$_2$). $^{31}$P{$^1$H} NMR (CDCl$_3$, 126 MHz) δ8.0.

Synthesis of borane-protected-((meso)-2,5-diphenylphospholan-1-yl)methanol 6, (meso)-6

Compound (meso)-6 was synthesized following literature procedures (L. Hintermann, M. Schmitz, O. V. Maltsev, P. Naumov, Synthesis, 2013, 45, 308-325).

Compound (meso)-10 (0.31 g, 1.20 mmol) and paraformaldehyde (0.43, 14.43 mmol) were suspended in methanol (15 mL). A solution of potassium hydroxide (0.24 g, 4.21 mmol) in methanol (15 mL) was added slowly. The reaction mixture was left to stir at room temperature for 16 hours. The reaction mixture was partitioned between ethyl acetate (100 mL) and water (100 mL). The organic products were collected and the aqueous layer was washed with ethyl acetate (2×50 mL). The organic products in ethyl acetate/methanol were combined, washed with brine, dried using magnesium sulfate and concentrated in vacuo. The crude product was purified by column chromatography on silica gel (silica 60, 40-63 μm) using 20% hexane in dichloromethane as eluent to afford compound (meso)-6 as a white solid (0.25 g, 0.89 mmol, 89%). $^1$H NMR (CDCl$_3$, 400 MHz) δ 7.52-7.26 (m, 10H, Ar—H), 3.84 (q, J=7.8, 7.0 Hz, 2H, O—CH$_2$—P), 3.38 (s, 2H), 2.87-2.66 (m, 2H, 2×P—CH—Ar), 2.51 (m, 2.7 Hz, 2H, 2×Ar—CH—CH$_2$), 0.64 (s, 3H, BH$_3$). $^{13}$C NMR (CDCl$_3$, 101 MHz) δ 136.11 (s, ArC), 136.06 (s, ArC), 129.02 (m, 4C, ArCH), 127.39 (m, 6C, ArCH), 56.21 (d, J=28.3 Hz, O—CH$_2$—P), 44.13 (d, J=26.8 Hz, 2C, CH—P), 31.37 (s, 2C, CH—CH$_2$). $^{31}$P{$^1$H} NMR (CDCl$_3$, 126 MHz) δ 49.2 (d, J=61.9 Hz).

Synthesis of 4,8-di-tert-butyl-6-(((meso)-2,5-diphenylphospholan-1-yl)methoxy)-2,10-dimethoxydibenzo[d,f][1,3,2]dioxaphosphepine 2, (tropos, meso)-2

Unless stated otherwise, the procedure was carried out under Ar. Diphenol 5 (0.20 g, 0.56 mmol) was suspended in toluene (7 mL) and triethylamine (0.19 mL, 1.35 mmol) was added. The solution was then cooled to 0° C., before a solution of phosphorus tribromide (0.06 mL, 0.68 mmol) in toluene (4 mL) was added slowly. The reaction was left to stir at room temperature for 16 hours. Insoluble salts were filtered out via cannula and the filtrate was concentrated in vacuo. The resultant solid was dissolved in toluene (5 mL) and added to a solution of compound (meso)-6 (0.16 g, 0.56 mmol) in toluene (5 mL). 1,4-diazabicyclo[2.2.2]octane (0.32 g, 2.82 mmol) in toluene (5 mL) was added slowly. The reaction was left to stir at room temperature for 16 hours. The reaction mixture was filtered through a short pad of silica gel (silica 60, 40-63 μm), eluted with toluene. The filtrate was concentrated in vacuo to afford a crude solid. The crude product was purified by column chromatography on silica gel (silica 60, 40-63 μm, pretreated with a solution of 95:5 toluene:triethylamine) using 0-10% diethyl ether in hexane as eluent under N$_2$, followed by preparative TLC with alumina on glass plates (neutral) using 15% diethyl ether in hexane as eluent to afford compound (tropos, meso)-2 as a white solid (0.12 g, 0.19 mmol, 33%). $^1$H NMR (CDCl$_3$, 500 MHz) δ 7.27-7.20 (m, 8H, Ar—H), 7.19-7.11 (m, 2H, Ar—H), 6.87 (d, J=3.1 Hz, 2H, Ar—H), 6.61 (d, J=3.1 Hz, 2H, Ar—H), 3.86 (s, 6H, 2×O—CH$_3$), 3.75 (m, 2H, 2×O—CH$_2$—P), 3.62 (d, J=5.7 Hz, 2H, 2×Ar—CH—CH$_2$), 2.34 (m, 4H, 2×Ar—CH—CH$_2$), 1.34 (s, 18H, 6×CH$_3$). $^{13}$C NMR (CDCl$_3$, 101 MHz) δ 155.17 (s, 2C, ArC—OCH$_3$), 142.22 (m, 2C, ArC—O—P), 141.93 (s, 2C, ArC—CCH$_3$), 138.98 (s, 2C, ArC), 133.12 (m, 2C, ArC—CH—P), 128.48 (s, 4C, ArCH), 127.39 (s, 2C, ArCH), 127.35 (s, 2C, ArCH), 125.96 (s, 2C, ArCH), 114.41 (s, 2C, ArCH), 112.49 (s, 2C, ArCH), 58.84 (d, J=19.8 Hz, O—CH$_2$—P), 55.53 (s, 2C, OCH$_3$), 46.04 (d, J=16.9 Hz, 2C, CH—P), 35.23 (s, 2C, ArC—C(CH$_3$)$_3$), 31.87 (m, 2C, CH—CH$_2$), 30.77 (s, 6C, ArC—C(CH$_3$)$_3$). $^{31}$P{$^1$H} NMR (CDCl$_3$, 126 MHz) δ 133.1 (s); 6.1 (s). HRMS (ES$^+$) C$_{39}$H$_{46}$O$_5$P$_2$— [M+H]$^+$ m/z: 657.2886 found, 657.2899 required.

Synthesis of 4,8-di-tert-butyl-6-(((trans)-2,5-diphenylphospholan-1-yl)methoxy)-2,10-dimethoxy-dibenzo[d,f][1,3,2]dioxaphosphepine 2, (tropos, trans)-2

Unless stated otherwise, the procedure was carried out under Ar. Biphenol 5 (0.33 g, 0.91 mmol) was suspended in toluene (5 mL) and triethylamine (0.38 mL, 2.74 mmol) was added. The solution was then cooled to 0° C., before a solution of phosphorus tribromide (0.10 mL, 1.10 mmol) in toluene (5 mL) was added slowly. The reaction was left to stir at room temperature for 16 hours. Insoluble salts were filtered out via cannula and the filtrate was concentrated in vacuo. The resultant solid was dissolved in toluene (5 mL) and added to a solution of compound (trans-Rac)-6 (0.28 g, 0.99 mmol) in toluene (5 mL). 1,4-diazabicyclo[2.2.2]octane (0.56 g, 4.95 mmol) in toluene (5 mL) was added slowly. The reaction was left to stir at room temperature for 16 hours. The reaction mixture was filtered through a short pad of silica gel (silica 60, 40-63 μm), eluted with toluene. The filtrate was concentrated in vacuo to afford a crude solid. The crude product was purified by column chromatography on silica gel (silica 60, 40-63 μm, pretreated with a solution of 95:5 toluene:triethylamine) using 0-20% diethyl ether in hexane as eluent under N$_2$, followed by preparative TLC with alumina on glass plates (neutral) using 20% diethyl ether in hexane as eluent to afford compound (tropos,trans)-2 as a white solid (0.10 g, 0.16 mmol, 17%). $^1$H NMR (CDCl$_3$, 500 MHz) δ 7.36-7.17 (m, 10H, Ar—H), 6.98 (dd, J=10.8, 3.1 Hz, 2H, Ar—H), 6.73 (dd, J=10.8, 3.1 Hz, 2H, Ar—H), 3.92-3.80 (m, 8H, 2×O—CH$_3$, P—CH$_2$—O), 3.69-3.60 (m, 2H, 2×P—CH—Ar), 2.64-2.55 (m, 1H, Ar—CH—CH$_2$), 2.37-2.29 (m, 2H, Ar—CH—CH$_2$), 2.00-1.84 (m, 1H, Ar—CH—CH$_2$), 1.42 (s, 9H, 3×CH$_3$), 1.38 (s, 9H, 3×CH$_3$). $^{13}$C NMR (CDCl$_3$, 126 MHz) δ 155.57 (s, ArC—OCH$_3$), 155.47 (s, ArC—OCH$_3$), 144.15 (s, ArC—CCH$_3$), 144.01 (s, ArC—CCH$_3$), 142.14 (m, 2C, ArC—O—P), 138.04 (m, 2C, ArC—CH—P), 133.49 (m, ArC), 133.34 (m, ArC), 128.48 (m, 4C, ArCH), 127.94 (s, ArCH), 127.87 (s, ArCH), 127.42 (s, ArCH), 127.39 (s, ArCH), 125.88 (m, 2C, ArCH), 114.55 (s, ArCH), 114.37 (s, ArCH), 112.74 (s, ArCH), 112.54 (s, ArCH), 62.31 (d, J=29.0 Hz, O—CH$_2$—P), 55.59 (s, 2C, OCH$_3$), 46.10 (d, J=13.6 Hz, CH—P), 45.78 (d, J=15.5 Hz, CH—P), 36.74 (s, CH—CH$_2$), 35.32 (s, 2C, ArC—CCH$_3$), 32.80 (s, CH—CH$_2$), 30.84 (s, 6C, ArC—CCH$_3$). $^{31}$P{$^1$H} NMR (CDCl$_3$, 126 MHz) δ 136.6 (s); 9.7 (s). HRMS (ES$^+$) C$_{39}$H$_{46}$O$_5$P$_2$— [M+H]$^+$ m/z: 657.2888 found, 657.2899 required.

Synthesis of 4,8-di-tert-butyl-6-(((2R,5R)-2,5-diphenylphospholan-1-yl)methoxy)-2,10-dimethoxy-dibenzo[d,f][1,3,2]dioxaphosphepine 2, (tropos,R,R)-2

Unless stated otherwise, the procedure was carried out under Ar. Biphenol 5 (0.75 g, 2.10 mmol) was suspended in toluene (10 mL) and triethylamine (0.97 mL, 6.93 mmol) was added. The solution was then cooled to 0° C., before a solution of phosphorus tribromide (0.30 mL, 3.15 mmol) in toluene (5 mL) was added slowly. The reaction was left to stir at room temperature for 16 hours. Insoluble salts were filtered out via cannula and the filtrate was concentrated in vacuo. The resultant solid was dissolved in toluene (5 mL) and added to a solution of compound (R,R)-6 (0.42 g, 1.47 mmol) in toluene (5 mL). 1,4-diazabicyclo[2.2.2]octane (0.82 g, 7.35 mmol) in toluene (5 mL) was added slowly. The reaction was left to stir at room temperature for 16 hours. The reaction mixture was filtered through a short pad of silica gel (silica 60, 40-63 μm), eluted with toluene. The filtrate was concentrated in vacuo to afford a crude solid. The crude product was purified by column chromatography on silica gel (silica 60, 40-63 μm, pretreated with a solution of 95:5 toluene:triethylamine) using 0-20% diethyl ether in hexane as eluent under N$_2$, followed by preparative TLC with alumina on glass plates (neutral) using 10% diethyl ether in hexane as eluent to afford compound (tropos,R,R)-2 as a white solid (0.20 g, 0.31 mmol, 21%). $^1$H NMR (CDCl$_3$, 500 MHz) δ 7.37-7.17 (m, 10H, Ar—H), 6.98 (dd, J=8.8, 3.1 Hz, 2H, Ar—H), 6.74 (dd, J=8.8, 3.1 Hz, 2H, Ar—H), 3.93-3.80 (m, 8H, 2×O—CH$_3$, P—CH$_2$—O), 3.71-3.59 (m, 2H, 2×P—CH—Ar), 2.66-2.54 (m, 1H, Ar—CH—CH$_2$), 2.38-2.29 (m, 2H, Ar—CH—CH$_2$), 2.01-1.87 (m, 1H, Ar—CH—CH$_2$), 1.42 (s, 9H, 3×CH$_3$), 1.38 (s, 9H, 3×CH$_3$). $^{13}$C NMR (CDCl$_3$, 101 MHz) δ 155.54 (s, ArC—OCH$_3$), 155.45 (s, ArC—OCH$_3$), 144.15 (s, ArC—CCH$_3$), 143.98 (s, ArC—CCH$_3$), 142.13 (m, 2C, ArC—O—P), 138.03 (m, 2C, ArC—CH—P), 133.48 (s, ArC), 133.34 (s, ArC), 128.46 (m, 4C, ArCH), 127.93 (s, ArCH), 127.85 (s, ArCH), 127.41 (s, ArCH), 127.37 (s, ArCH), 125.86 (m, 2C, ArCH), 114.53 (s, ArCH), 114.35 (s, ArCH), 112.74 (s, ArCH), 112.53 (s, ArCH), 62.28 (d, J=29.1 Hz, O—CH$_2$—P), 55.60 (s, 2C, OCH$_3$), 46.09 (d, J=13.6 Hz, CH—P), 45.76 (d, J=15.5 Hz, CH—P), 36.72 (s, CH—CH$_2$), 35.33 (s, 2C, ArC—C(CH$_3$)$_3$), 32.79 (s, CH—CH$_2$), 30.80 (s, 6C, ArC—C(CH$_3$)$_3$). $^{31}$P{$^1$H} NMR (CDCl$_3$, 126 MHz) δ 136.6 (s); 9.7 (s). HRMS (ES$^+$) C$_3$H$_{46}$O$_5$P$_2$— [M+]$^+$ m/z: 657.2884 found, 657.2899 required.

Synthesis of 3,3'-di-tert-butyl-5,5'-dimethyl-[1,1'-biphenyl]-2,2'-diol 8

The commercially available 2-(tert-butyl)-4-methylphenol 7 (1.63 g, 9.93 mmol) was dissolved in heptane (10 mL). To this was added manganese oxide (1.15 g, 13.24 mmol) and the mixture was heated to reflux for 1.5 hours. The reaction mixture was filtered through celite and the filtrate was concentrated in vacuo. The crude product was purified by column chromatography on silica gel (silica 60, 40-63 μm) using 10% diethyl ether in hexane as eluent to afford compound 8 as a pale yellow solid (1.02 g, 3.13 mmol, 63%). $^1$H NMR (CDCl$_3$, 400 MHz) δ 7.20 (d, J=2.1 Hz, 2H, 2×Ar—H), 6.95 (d, J=2.1 Hz, 2H, 2×Ar—H), 5.23 (s, 2H, 2×OH), 2.36 (s, 6H, 2×Ar-CH$_3$), 1.49 (s, 18H, 2×Ar-C(CH$_3$)$_3$). $^{13}$C NMR (CDCl$_3$, 101 MHz) δ 149.87 (s, 2C, 2×ArC—OH), 136.91 (s, 2C, 2×ArC—C(CH$_3$)$_3$), 129.57 (s, 2C, 2×ArC—CH$_3$), 128.78 (s, 2C, 2×ArCH), 128.48 (s, 2C, 2×ArCH), 122.57 (s, 2C, 2×ArC—ArC), 34.93 (s, 2C, 2×C(CH$_3$)$_3$), 29.66 (s, 6C, 2×C(CH$_3$)$_3$), 20.84 (s, 2C, 2×Ar-CH$_3$). HRMS (ES$^+$) C$_{22}$H$_{30}$O$_2$— [M−H]$^-$ m/z: 325.2171 found, 325.2173 required.

Synthesis of 4,8-di-tert-butyl-6-(((2R,5R)-2,5-diphenylphospholan-1-yl)methoxy)-2,10-dimethyldibenzo[d,f][1,3,2]dioxaphosphepine 3, (tropos,R,R)-3

Unless stated otherwise, the procedure was carried out under Ar. Biphenol 8 (0.40 g, 1.23 mmol) was suspended in toluene (10 mL) and triethylamine (0.64 mL, 4.62 mmol) was added. The solution was then cooled to 0° C., before a solution of phosphorus tribromide (0.17 mL, 1.85 mmol) in toluene (5 mL) was added slowly. The reaction was left to stir at room temperature for 16 hours. Insoluble salts were filtered out via cannula and the filtrate was concentrated in vacuo. The resultant solid was dissolved in toluene (5 mL) and added to a solution of compound (R,R)-6 (0.35 g, 1.23 mmol) in toluene (5 mL). 1,4-diazabicyclo[2.2.2]octane (0.69 g, 6.15 mmol) in toluene (10 mL) was added slowly. The reaction was left to stir at room temperature for 16 hours. The reaction mixture was filtered through a short pad of silica gel (silica 60, 40-63 µm), eluted with toluene. The filtrate was concentrated in vacuo to afford a crude solid. The crude product was purified by preparative TLC with alumina on glass plates (neutral) using hexane as eluent to afford compound (tropos,R,R)-3 as a white solid (0.08 g, 0.12 mmol, 10%). $^1$H NMR (CDCl$_3$, 500 MHz) δ 7.36-7.15 (m, 12H, Ar—H), 7.02-6.97 (m, 2H, Ar—H), 3.89-3.83 (m, 2H, P—CH$_2$—O), 3.70-3.58 (m, 2H, 2×P—CH—Ar), 2.63-2.52 (m, 1H, P—CH—CH$_2$), 2.42 (s, 3H, Ar—CH$_3$), 2.39 (s, 3H, Ar—CH$_3$), 2.36-2.28 (m, 2H, P—CH—CH$_2$), 1.99-1.87 (m, 1H, P—CH—CH$_2$), 1.40 (s, 9H, C(CH$_3$)$_3$), 1.38 (s, 9H, C(CH$_3$)$_3$). $^{13}$C NMR (CDCl$_3$, 101 MHz) δ 146.40 (m, 2C, ArC—O—P), 144.25 (s, ArC—CCH$_3$), 144.07 (s, ArC—CCH$_3$), 140.31 (s, ArC—CH—P), 138.12 (s, ArC—CH—P), 133.28 (s, ArC), 133.14 (s, ArC), 132.73 (s, 2C, ArC—CH$_3$), 129.96 (s, ArCH), 129.87 (s, ArCH), 128.47 (m, 4C, ArCH), 127.97 (m, 4C, ArCH), 127.50 (s, 2C, ArCH), 125.88 (s, 2C, ArCH), 62.19 (d, J=29.4 Hz, O—CH$_2$—P), 46.18 (d, J=13.7 Hz, CH—P), 45.63 (d, J=15.4 Hz, CH—P), 36.73 (s, CH—CH$_2$), 35.06 (s, 2C, ArC—C(CH$_3$)$_3$), 32.83 (s, CH—CH$_2$), 31.02 (s, 6C, ArC—C(CH$_3$)$_3$), 21.22 (s, 2C, ArC—CH$_3$). $^{31}$P{$^1$H} NMR (CDCl$_3$, 126 MHz) δ 136.5 (s); 10.2 (s). HRMS (ES$^+$) C$_{39}$H$_{46}$O$_3$P$_2$— [M+H]$^+$ m/z: 625.2990 found, 625.3000 required.

Synthesis of 4,8-di-tert-butyl-6-(((trans)-2,5-diphenylphospholan-1-yl)methoxy)-2,10-dimethyldibenzo[d,f][1,3,2]dioxaphosphepine 3, (tropos,trans)-3

Unless stated otherwise, the procedure was carried out under Ar. Diphenol 8 (0.24 g, 0.72 mmol) was suspended in toluene (7 mL) and triethylamine (0.24 mL, 1.73 mmol) was added. The solution was then cooled to 0° C., before a solution of phosphorus tribromide (0.08 mL, 0.86 mmol) in toluene (4 mL) was added slowly. The reaction was left to stir at room temperature for 16 hours. Insoluble salts were filtered out via cannula and the filtrate was concentrated in vacuo. The resultant solid was dissolved in toluene (5 mL) and added to a solution of compound (trans)-6 (0.20 g, 0.72 mmol) in toluene (5 mL). 1,4-diazabicyclo[2.2.2]octane (0.40 g, 3.60 mmol) in toluene (5 mL) was added slowly. The reaction was left to stir at room temperature for 16 hours. The reaction mixture was filtered through a short pad of silica gel (silica 60, 40-63 µm), eluted with toluene. The filtrate was concentrated in vacuo to afford a crude solid. The crude product was purified by column chromatography on silica gel (silica 60, 40-63 µm, pretreated with a solution of 95:5 toluene:tnethylamine) using hexane as eluent under N$_2$, followed by preparative TLC with alumina on glass plates (neutral) using 10% diethyl ether in hexane as eluent to afford compound (tropos,trans)-3 as a white solid (0.10 g, 0.15 mmol, 21%). $^1$H NMR (CDCl$_3$, 400 MHz) δ 7.40-7.33 (m, 4H, Ar—H), 7.32-7.18 (m, 8H, Ar—H), 7.05-7.02 (m, 2H, Ar—H), 3.94-3.81 (m, 2H P—CH$_2$—O), 3.75-3.61 (m, 2H, 2×P—CH—Ar), 2.68-2.56 (m, 1H, P—CH—CH$_2$), 2.47-2.45 (m, 3H, Ar—CH$_3$), 2.44-2.41 (m, 3H, Ar—CH$_3$), 2.40-2.31 (m, 2H, P—CH—CH$_2$), 2.02-1.89 (m, 1H, P—CH—CH$_2$), 1.45 (s, 9H, C(CH$_3$)$_3$), 1.42 (s, 9H, C(CH$_3$)$_3$). $^{13}$C NMR (CDCl$_3$, 101 MHz) δ 146.32 (m, 2C, ArC—O—P), 144.26 (s, ArC—CCH$_3$), 144.08 (s, ArC—CCH$_3$), 140.31 (m, ArC—CH—P), 138.14 (s, ArC—CH—P), 133.29 (s, ArC), 133.15 (s, ArC), 132.75 (m, 2C, ArC—OCH$_3$), 129.98 (s, 2C, ArCH), 129.89 (s, 2C, ArCH), 128.48 (m, 4C, ArCH), 127.99 (m, 4C, ArCH), 127.51 (s, ArCH), 127.48 (s, ArCH), 125.89 (s, ArCH), 125.84 (s, ArCH), 62.22 (d, J=29.4 Hz, O—CH$_2$—P), 46.20 (d, J=13.7 Hz, CH—P), 45.67 (d, J=15.4 Hz, CH—P), 36.74 (s, CH—CH$_2$), 35.08 (s, 2C, ArC—C(CH$_3$)$_3$), 32.88 (s, CH—CH$_2$), 31.05 (s, 6C, ArC—C(CH$_3$)$_3$), 21.24 (s, ArC—CH$_3$), 21.20 (s, ArC—CH$_3$). $^{31}$P{$^1$H} NMR (CDCl$_3$, 126 MHz) δ 136.5 (s); 10.2 (s). HRMS (ES$^+$) C$_{39}$H$_{46}$O$_3$P$_2$— [M+H]$^+$ m/z: 625.2997 found, 625.3000 required.

Synthesis of 4,8-di-tert-butyl-6-(((meso)-2,5-diphenylphospholan-1-yl)methoxy)-2,10-dimethoxy-dibenzo[d,f][1,3,2]dioxaphephine 2, (tropos, meso)-2

Unless stated otherwise, the procedure was carried out under Ar. Diphenol 5 (0.20 g, 0.56 mmol) was suspended in toluene (7 mL) and triethylamine (0.19 mL, 1.35 mmol) was added. The solution was then cooled to 0° C., before a solution of phosphorus tribromide (0.06 mL, 0.68 mmol) in toluene (4 mL) was added slowly. The reaction was left to stir at room temperature for 16 hours. Insoluble salts were filtered out via cannula and the filtrate was concentrated in vacuo. The resultant solid was dissolved in toluene (5 mL) and added to a solution of compound (meso)-6 (0.16 g, 0.56 mmol) in toluene (5 mL). 1,4-diazabicyclo[2.2.2]octane (0.32 g, 2.82 mmol) in toluene (5 mL) was added slowly. The reaction was left to stir at room temperature for 16 hours. The reaction mixture was filtered through a short pad of silica gel (silica 60, 40-63 µm), eluted with toluene. The filtrate was concentrated in vacuo to afford a crude solid. The crude product was purified by column chromatography on silica gel (silica 60, 40-63 µm, pretreated with a solution of 95:5 toluene:triethylamine) using 0-10% diethyl ether in hexane as eluent under N$_2$, followed by preparative TLC with alumina on glass plates (neutral) using 15% diethyl ether in hexane as eluent to afford compound (tropos, meso)-2 as a white solid (0.12 g, 0.19 mmol, 33%). $^1$H NMR (CDCl$_3$, 500 MHz) δ 7.27-7.20 (m, 8H, Ar—H), 7.19-7.11 (m, 2H, Ar—H), 6.87 (d, J=3.1 Hz, 2H, Ar—H), 6.61 (d, J=3.1 Hz, 2H, Ar—H), 3.86 (s, 6H, 2×O—CH$_3$), 3.75 (m, 2H, 2×O—CH$_2$—P), 3.62 (d, J=5.7 Hz, 2H, 2×Ar—CH—CH$_2$), 2.34 (m, 4H, 2×Ar—CH—CH$_2$), 1.34 (s, 18H, 6×CH$_3$). $^{13}$C NMR (CDCl$_3$, 101 MHz) δ 155.17 (s, 2C, ArC—OCH$_3$), 142.22 (m, 2C, ArC—O—P), 141.93 (s, 2C, ArC—CCH$_3$), 138.98 (s, 2C, ArC), 133.12 (m, 2C, ArC—CH—P), 128.48 (s, 4C, ArCH), 127.39 (s, 2C, ArCH), 127.35 (s, 2C, ArCH), 125.96 (s, 2C, ArCH), 114.41 (s, 2C, ArCH), 112.49 (s, 2C, ArCH), 58.84 (d, J=19.8 Hz, O—CH$_2$—P), 55.53 (s, 2C, OCH$_3$), 46.04 (d, J=16.9 Hz, 2C, CH—P), 35.23 (s, 2C, ArC—C(CH$_3$)$_3$), 31.87 (m, 2C, CH—CH$_2$), 30.77 (s, 6C, ArC—C(CH$_3$)$_3$). $^{31}$P{$^1$H} NMR (CDCl$_3$, 126 MHz) δ 133.1 (s); 6.1 (s). HRMS (ES$^+$) C$_{39}$H$_{46}$P$_2$— [M+H]$^+$ m/z: 657.2886 found, 657.2899 required.

Synthesis of (atropos,R,R,R)-1/(atropos,S,S,S)-1 mixture

Procedure was adapted from the synthesis of (S$_{ax}$,S,S)-BOBPHOS (P. Dingwall, J. A. Fuentes, L. Crawford, A. M. Z. Slawin, M. Bühl, M. L. Clarke, *J. Am. Chem. Soc.*, 2017, 139, 15921)

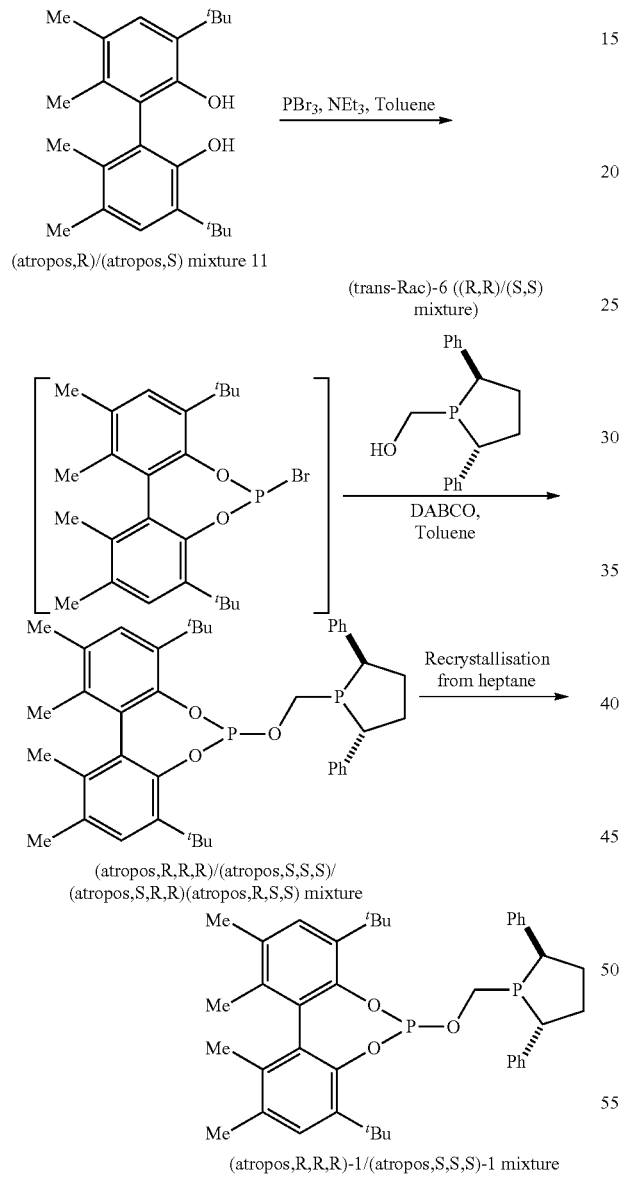

Unless stated otherwise, the procedure was carried out under Ar. Biphenol 11 (as the R$_{ax}$/S$_{ax}$ mixture) (0.37 g, 1.06 mmol) was suspended in toluene (10 mL) and triethylamine (0.37 mL, 2.66 mmol) was added. The solution was then cooled to 0° C., before a solution of phosphorus tribromide (0.12 mL, 1.27 mmol) in toluene (5 mL) was added slowly. The reaction was left to stir at room temperature for 16 hours. Insoluble salts were filtered out via cannula and the filtrate was concentrated in vacuo. The resultant solid was dissolved in toluene (5 mL) and added to a solution of ((trans)-2,5-diphenylphospholan-1-yl)methanol 6 (as the (R,R)/(S,S) mixture) (0.30 g, 1.06 mmol) in toluene (5 mL). 1,4-diazabicyclo[2.2.2]octane (0.47 g, 4.23 mmol) in toluene (5 mL) was added slowly. The reaction was left to stir at room temperature for 16 hours. The reaction mixture was filtered through a short pad of silica gel (silica 60, 40-63 μm), eluted with toluene. The filtrate was concentrated in vacuo to afford a crude solid (as an equal mixture of (R$_{ax}$,R,R)/(R$_{ax}$,S,S)/(S$_{ax}$,R,R)/(S$_{ax}$,S,S) isomers). The crude product was purified by recrystallisation from heptane to afford compound (as the (R$_{ax}$,R,R)/(S$_{ax}$,S,S) mixture) as a white solid (0.12 g, 0.16 mmol, 18%). The spectral data are in agreement with the full characterisation data of the (S$_{ax}$,S,S) enantiomer previously reported. (Noonan, Fuentes, Cobley, Clarke, Angew. Chem. Int. Ed. 2012, 51, 2477)

What is claimed is:

1. A process for preparing at least one aldehyde under hydroformylation temperature and pressure conditions, comprising contacting at least one olefin with hydrogen and carbon monoxide in the presence of at least one hydrocarbon solvent comprising n-nonane, n-decane, n-undecane, or n-dodecane, and a transition metal-based catalyst composition comprising a phospholane phosphite ligand represented by the following general formula:

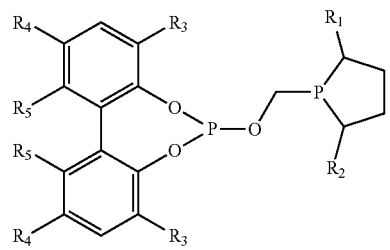

wherein:
R1 and R2 are independently selected from substituted and unsubstituted, aryl, alkyl, aryloxy or cycloalkyl groups containing from 1 to 40 carbon atoms;
R3 and R4 are independently selected from substituted and unsubstituted, aryl, alkyl, alkoxy, trialkylsilyl, triarylsilyl, aryldialkylsilyl diarylalkylsilyl and cycloalkyl groups containing from 1 to 20 carbon atoms, wherein the silicon atom of the alkylsilyl is in the alpha position of the substituent; and
R5 is independently selected from H, or alkyl group.

2. The process of claim 1, wherein the phospholane phosphite ligand is represented by the following general formula:

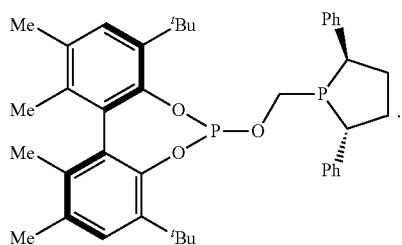

3. The process of claim 1, wherein the product of the process comprises an iso-selectivity of about 55% to about 80%.

4. The process of claim 1, wherein the product of the process comprises an iso-selectivity of about 58 to about 73%.

5. The process of claim 1, wherein the product of the process comprises an iso-selectivity of about 60 to about 70%.

6. The process of claim 1, wherein the product of the process comprises an iso-selectivity of 55% or greater.

7. The process of claim 1, wherein the pressure ranges from about 2 atm to about 80 atm.

8. The process of claim 7, wherein the pressure ranges from about 8 atm to about 20 atm.

9. The process of claim 1, wherein the pressure is about 8 atm.

10. The process of claim 1, wherein the pressure is about 20 atm.

11. The process of claim 1, wherein the temperature ranges from about 40 about 120 degrees Celsius.

12. The process of claim 1, wherein the temperature ranges from about 50 about 90 degrees Celsius.

13. The process of claim 1, wherein the temperature is about 50 degrees Celsius.

14. The process of claim 1, wherein the temperature is about 75 degrees Celsius.

15. The process of claim 1, wherein the temperature is about 90 degrees Celsius.

16. The process of claim 1, wherein the olefin comprises propylene.

17. The process of claim 1, wherein the transition metal based catalyst comprises a rhodium based catalyst.

18. A process for preparing at least one aldehyde under hydroformylation temperature and pressure conditions, comprising contacting at least one olefin with hydrogen and carbon monoxide in the presence of at least one hydrocarbon solvent comprising n-nonane, n-decane, n-undecane, or n-dodecane, and a transition metal-based catalyst composition comprising a phospholane phosphite ligand derived from an achiral biphenol diol component.

19. The process of claim 18, wherein the phospholane phosphite ligand derived from the achiral biphenol diol component is selected from the following ligands, (A) through (D), represented by their general formulas:

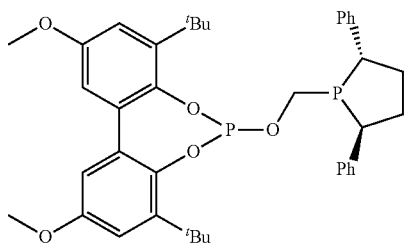

(A)

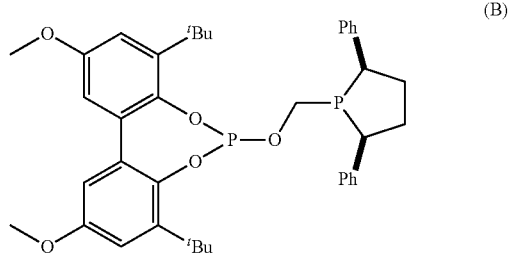

(B)

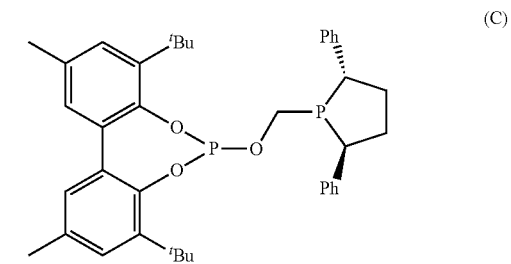

(C)

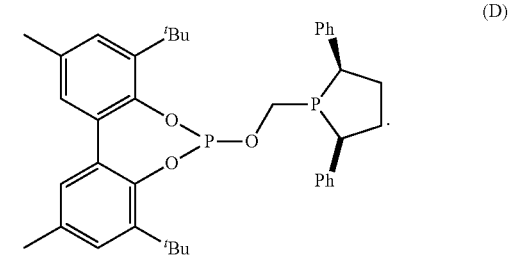

(D)

20. The process of claim 18, wherein the product of the process comprises an iso-selectivity of about 55% to about 80%.

21. The process of claim 18, wherein the product of the process comprises an iso-selectivity of 55% or greater.

22. The process of claim 18, wherein the pressure ranges from about 2 atm to about 80 atm.

23. The process of claim 18, wherein the temperature ranges from about 40 about 120 degrees Celsius.

24. The process of claim 18, wherein the olefin comprises propylene.

25. The process of claim 18, wherein the transition metal based catalyst comprises a rhodium based catalyst.

* * * * *